United States Patent [19]

Falkowski et al.

[11] 4,294,958
[45] Oct. 13, 1981

[54] WATER-SOLUBLE SALTS OF TRIMETHYLAMMONIUM DERIVATIVES OF POLYENE MACROLIDE ANTIBIOTICS AND THE PREPARATION THEREOF

[75] Inventors: Leonard Falkowski, Gdańsk; Barbara Stefanska, Gdańsk-Oliwa; Jan Zielinski, Gdańsk-Oliwa; Elzbieta Troka, Gdańsk-Oliwa; Jerzy Golik, Sopot; Pawel Kolodziejczyk, Gdańsk-Wrzeszcz; Andrzej Jarzebski, Gdańsk; Emilia Cybulska, Gdańsk-Oliwa; Edward Borowski, Gdańsk-Wrzeszcz all of Poland

[73] Assignee: Politechnika Gdanska, Gdansk, Poland

[21] Appl. No.: 60,427

[22] Filed: Jul. 25, 1979

[30] Foreign Application Priority Data

Jul. 19, 1978 [PL] Poland .................................. 208519

[51] Int. Cl.³ .............................................. C07H 17/08
[52] U.S. Cl. .................................... 536/17 R; 424/180
[58] Field of Search ........................ 536/17 R, 17 C

[56] References Cited

U.S. PATENT DOCUMENTS

| 4,035,568 | 7/1977 | Schaffner et al. | 536/17 |
| 4,041,232 | 8/1977 | Sipos et al. | 536/17 |
| 4,144,328 | 3/1979 | Vainshtein et al. | 536/17 |

*Primary Examiner*—Delbert R. Phillips
*Assistant Examiner*—Blondel Hazel
*Attorney, Agent, or Firm*—Ladas & Parry

[57] ABSTRACT

Inorganic salts of trimethylammonium derivatives of polyene macrolides, particularly the inorganic salts of methyl esters of these derivatives having the general formula:

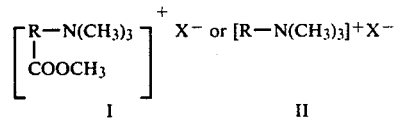

wherein R is the residue of a polyene macrolide and X is an anion of a salt selected from the group consisting of methylsulphate, sulphate, chloride, phosphate and acetate.

The preparation of salts of formula (I) or formula (II) is also disclosed.

4 Claims, No Drawings

WATER-SOLUBLE SALTS OF TRIMETHYLAMMONIUM DERIVATIVES OF POLYENE MACROLIDE ANTIBIOTICS AND THE PREPARATION THEREOF

FIELD OF THE INVENTION

This invention relates to water-soluble salts of trimethylammonium derivatives of polyene macrolides, particularly the water-soluble salts of methyl esters of the said derivatives.

The invention is also concerned with a process for the preparation of such salts.

The polyene macrolide antibiotics are commonly applied in therapy of fungal infections of men and animals and in the prevention or elimination of fungal contaminations of various materials.

DESCRIPTION OF THE PRIOR ART

A number of derivatives of polyene macrolides exhibiting some properties more desirable than the parent antibiotics is already known. Known is the complex of amphotericin B. with sodium deoxycholate, the N-acyl derivatives of polyene macrolides /U.S. Pat. No. 3,244,570 /1966/, the hydrochlorides of methyl esters of polyene macrolides/Mechlinski W., Schaffner C. P.; J. Antibiot. 25, 256 /1964/, the product of condensation of formaldehyde with candidin /France Per., Rhone-Poulene 41.272/ or products of reaction of polyene macrolides with polysaccharides oxygenated upon treatment with periodate /Belgium Pat. 620619/ and the N-glycosyl derivatives of polyene macrolides /Belgium Pat. 787531/. However, the above described derivatives display some other undesirable properties, like: N-acyl polyene macrolides exhibit significant lower antifungal activity, the salts of methyl esters of these antibiotics are rather unstable.

U.S. Pat. No. 4,144,328 discloses N,N,N-trimethyl derivatives of polyene macrolide antibiotics selected from the group consisting of amphotericin B, nystatin and mycoheptin. The stated derivatives are not water soluble, which makes it difficult to administer them in solution form.

SUMMARY OF THE INVENTION

In accordance with the present invention there is provided an antibiotically-active water-soluble salt of a trimethylammonium derivative of a polyene macrolide having the general formula:

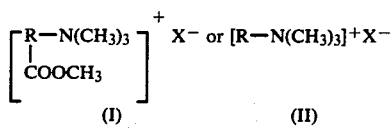

wherein R is the residue of a polyene macrolide selected from the group consisting of nystatin, polyfungin, amphotericin B, candicidin, pimaricin, trichomycin, levorin, rimocidin, candidin, aureofacin, perimycin and mycoheptin, and X is an anion of a salt selected from the group consisting of methylsulphate, sulphate, chloride, phosphate and acetate.

The invention also provides a process for the preparation of an antibiotically-active water-soluble salt of a trimethylammonium derivative of a polyene macrolide having the general formula:

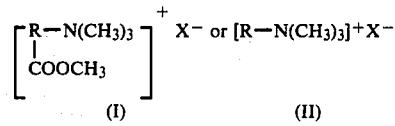

wherein R is the residue of a polyene macrolide selected from the group consisting of nystatin, polyfungin, amphotericin B, candicidin, pimaricin, trichomycin, levorin, rimocidin, candidin, aureofacin, perimycin and mycoheptin, and X is an anion of a salt selected from the group consisting of methylsulphate, sulphate, chloride, phosphate and acetate, which comprises reacting a solution of the polyene macrolide in an organic solvent with dimethylsulphate in the presence of a neutralizing agent at room temperature with continuous stirring until the reaction is substantially complete, precipitating the resulting methylsulphate of N,N,N-trimethyl polyene macrolide methyl ester of formula (I) or methylsulphate of N,N,N-trimethyl polyene macrolide of formula (II) by the addition of ethyl ether in butanol, washing the organic solvent with water and concentrating under reduced pressure the resulting solution of the desired product of formula (I) or (II) in the form of the dimethylsulphate salt thereof and, if desired, converting the dimethylsulphate salt into another salt as defined above.

DESCRIPTION OF THE PREFERRED EMBODIMENTS

Preferred organic solvents used in the process of the invention are dimethylacetamide, dimethylformamide, dimethylsulphoxide and aliphatic alcohols of chain length $C_1$–$C_5$.

The preferred neutralizing agent is sodium hydrogen carbonate.

In the polyene macrolides containing an aromatic amino group, this group is substituted with one or two methyls. Those antibiotics are represented by levorin, candicidin, trichomycin, aureofacin, perimycin.

The reaction conditions used in the process of the invention are sufficiently mild to prevent degradation of the antibiotics in contrast with treatment of the polyene macrolide with dimethylsulphate in conditions known in the prior art which resulted in opening of the macrolide ring, elimination of the sugar moiety and degradation of the polyene chromophore, resulting in loss of biological activity.

The in vitro antimicrobial and hemolytic activities of DMS polyene macrolides and the parent antibiotics comparatively are presented in the table 1.

The structure of obtained derivatives had been documented by means of spectroscopic methods. Exemplary are presented the procedure applied for identification of candicidin derivative, further designated as DMS candicidin, obtained upon treatment of the antibiotic with dimethylsulphate in the proposed conditions of alkilation. Acidic hydrolysis of candicidin itself yields the sugar moiety mycosamine, whereas DMS candicidin afforded N,N,N-trimethylmycosamine. The structure of that substance resulted from the field desorption mass spectrum /the base ions and simultaneously the molecular ions at m/e 206/ as well as from the proton magnetic resonance spectrum /signal al $\sigma = 3.68$ characteristic for the methyl groups attached to nitrogen atom of intensity three times higher than the signal at $\sigma = 1.68$ characteristic for the protons of C-6 methyl group of the aminosugar.

The presence of the ester bond in the molecule of the derivative is indicated by the intensive absorption bond at $\lambda=1730$ cm$^{-1}$ in the IR spectrum and coincident lack of the absorption at $\lambda=1590$ cm$^{-1}$ characteristic for the parent antibiotic. The electronic absorption of candicidin and its DMS derivative differ slightly in the intensities of absorption maxima, whereas their location and the ascilation structure of the spectrum are identical. This gave evidence that the structure of polyene chromophor remained unchanged in the procedure of alkilation. The NMR spectrum of per-O-trimethylsilyl-DMS-candicidin displayed bands at $\sigma=3.65$ and 3.03 characteristic for the methoxy and N-methyl protons respectively. Treatment of alkaline water solutions of candicidin released p-aminoacetophenone, whereas DMS-candicidin N-dimethyl, N-methyl and non substituted, p-aminoacetophenone in molar ratio 3:5:2.

The advantage of the derivatives described in our invention are their perfect water solubility together with high antifungal activity and improved selective toxity as compared to the native antibiotics.

The inorganic salts of trimethylammonium derivatives of polyene macrolides particularly the methyl esters of inorganic salts of trimethylammonium derivatives of these antibiotics and the method of their preparation is presented by the examples cited below:

EXAMPLE 1

2 g of polyfungin /$E_{1\ cm}^{1\%}=800$ at 304 nm/ is dissolved in 10 ml of dimethylformamide and 10 ml of methanol, 2 g sodium bicarbonate, and 1 ml of dimethylsulphate were added portionwise and the reaction mixture was stirred for 10 hrs at 25° C. The undissolved sodium hydrogen carbonate was centrifuged, and methanol evaporated under reduced pressure and the derivative was precipitated with ethyl ether. The product was dissolved in 50 ml of water saturated butanol, the butanol layer washed two times with 20 ml of water and concentrated under reduced pressure to 15 ml volume. Precipitation with ethyl ether, followed by washing two times with ethyl ether and hexane yielded 1.6 g of the salts of N,N,N-trimethylpolifungin methyl ester, displaying $E_{1\ cm}^{1\%}=700$ at 304 nm. The achieved yield is 80% of the theoretical.

EXAMPLE 2

2 g of nystatin /$E_{1\ cm}^{1\%}=860$ at 304 nm/ was dissolved in 50 ml of methanol, 2 g of sodium hydrogen carbonate was added and 2 ml of dimethylsulphate added portionwise. The reaction mixture was stirred four hrs at 25° C. and further worked up as described in example 1. The salt of N,N,N-trimethylnystatin methyl ester was obtained with yield 1.3 g /75% of the theoretical/, the product exhibited $E_{1\ cm}^{1\%}=760$ at 304 nm.

EXAMPLE 3

1 g of amphotericin B /$E_{1\ cm}^{1\%}=1420$ at 383 nm/ was dissolved in 20 ml of dimethylformamide—methanol in ratio 10:1 mixture, 1 g of sodium hydrogen carbonate was added and 1 ml of dimethylsulphate added. The reaction mixture was stirred at 20° C. 24 hours and further worked up as in example I: 0.9 g of the salt of N,N,N-trimethylamphotericin B methyl ester displaying $E_{1\ cm}^{1\%}=900$ at 382 nm was obtained, which makes 90% of theoretical yield. The obtained substance was purified by means of counter current distribution in solvent system: chloroform-methanol-water /2:2:1/. Obtained was 0.3 g of salt of N,N,N-trimethylamphotericin methyl ester displaying $E_{1\ cm}^{1\%}=1400$ at 382 nm.

EXAMPLE 4

1 g of candidin /$E_{1\ cm}^{1\%}=820$ at 383 nm was dissolved in 20 ml of dimethylformamide-methanol in ratio 10:1 mixture, 1 g of sodium hydrogen carbonate was added and 1 ml of dimethylsulphate added. The reaction mixture was stirred 15 hours at 20° C. and further worked up as in example I. Obtained was 0.5 g of the salt N,N,N-trimethylcandidin methyl ester displaying $E_{1\ cm}^{1\%}=550$ at 382 nm which makes 80% of theoretical yield. The product was purified by means of column chromatography in silica gel initially saturated with water in solvent system chloroform-methanol-water /20:10:1/. Obtained was 0.2 g of the derivative of candidin displaying $E_{1\ cm}^{1\%}=850$ at 378 nm.

EXAMPLE 5

1 g of trichomycin /$E_{1\ cm}^{1\%}=450$ at 378 nm/ was dissolved in 20 ml of dimethylformamide-methanol in ratio 10:1 mixture. 1 g of sodium hydrogen carbonate was added and 1 ml of dimethylsulphate added. The reaction mixture was stirred 15 hours at 20° C. and further worked up as in example I. Obtained was 0.6 g of DMS-trichomycin displaying $E_{1\ cm}^{1\%}=560$ at 378 nm.

EXAMPLE 6

1 g of pimaricin /$E_{1\ cm}^{1\%}=960$ at 304 nm/ was dissolved in 20 ml of methanol, 1 g of sodium hydrogen carbonate was added and 1 ml of dimethylsulphate was added. The reaction mixture was stirred 15 hours at 25° C. and further worked up as described in example I. Obtained was 0.85 g of the salt of N,N,N-trimethylammonium methyl ester displaying $E_{1\ cm}^{1\%}=700$ at 304 nm, which makes 80% of the theoretical yield.

EXAMPLE 7

1 g of levorin /$E_{1\ cm}^{1\%}=800$ at 378 nm/ was dissolved in 30 ml of dimethylformamide-methanol in ratio 10:1 mixture, 1 g of sodium hydrogen carbonate was added and 1 ml of dimethylsulphate added. The reaction mixture was stirred for 15 hours at 20° C. and further worked up as described in example I. Obtained was 0.7 g of DMS-levorin displaying $E_{1\ cm}^{1\%}=600$ at 304 nm which makes 70% of the theoretical yield.

EXAMPLE 8

1 g of rimocidin /$E_{1\ cm}^{1\%}=600$ at 304 nm/ was dissolved in 20 ml of dimethylformamide-methanol in ratio 10:1 mixture, 1 g of sodium hydrogen carbonate was added and 1 ml of dimethylsulphate added. The reaction mixture was stirred for 15 hours at 20° C. and further worked up as described in example I. Obtained was 0.8 g of the salt of N,N,N-trimethylrimocidin methyl ester displaying $E_{1\ cm}^{1\%}=560$ at 304 nm, which makes 80% of the theoretical yield.

EXAMPLE 9

0.1 g of perimycin /$E_{1\ cm}^{1\%}=650$ at 380 nm/ was dissolved in 2 ml of dimethylacetamide-methanol in ratio 10:1 mixture, 0.1 g sodium hydrogen carbonate was added, and 0.1 nl of dimethylsulphate added. The reaction mixture was stirred for 10 hours at 20° C. and further worked up as described in example I. 0.05 g of DMS-perimycin displaying $E_1\ _{cm}^{1\%} = 600$ at 380 nm which makes 50% of the theoretical yield.

EXAMPLE 10

1 g of aureofacin /$E_1\ _{cm}^{1\%} = 800$ at 379 nm/ was dissolved in dimethylformamide-methanol in ratio 10:1 mixture, 1 g of sodium hydrogen carbonate was added and 1 ml of dimethylsulphate added. The reaction mixture was stirred for 20 hours at 20° C. and further worked up as described in example I. Obtained was 0.7 g of DMS-aureofacin displaying $E_1\ _{cm}^{1\%} = 760$ at 378 nm which makes 65% of the theoretical yield.

EXAMPLE 11

0.1 g of candicidin /$E_1\ _{cm}^{1\%} = 400$ at 378 nm/ was dissolved in 5 ml of dimethylformamide-methanol in ratio 10:1 mixture and 0.1 g sodium hydrogen carbonate was added and 0.1 ml of dimethylsulphate added. The reaction mixture was stirred 15 hours at 20° C. and further worked up as described in example I. Obtained was 0.04 g of DMS-candicidin displaying $E_1\ _{cm}^{1\%} = 560$ at 378 nm which makes 45% of the theoretical yield.

EXAMPLE 12

1 g of mycoheptin /$E_1\ _{cm}^{1\%} = 700$ at 383 nm/ was dissolved in 20 ml of dimethylformamide-methanol in ratio 10:1 mixture, 1 g of sodium hydrogen carbonate was added and 1 ml dimethylsulphate added. The reaction mixture was stirred for 15 hours at 20° C. and further worked up as described in example I. Obtained was 0.5 g of the salt of N,N,N-dimethyl-mycoheptin methyl ester displaying $E_1\ _{cm}^{1\%} = 680$ at 380 nm, which makes 85% of the theoretical yield.

TABLE

The antifungal and haemolytic activities of polyene macrolides and their DMS derivatives

| Antibiotic | IC$_{50}$ / mcg/ml / | EH$_{50}$ / mcg/ml / |
|---|---|---|
| Pimaricin | 1 | 100 |
| DMS-Pimaricin | 1.7 | 400 |
| Polifungin | 0.08 | 20 |
| DMS-Polifungin | 0.15 | 120 |
| Nystatin | 0.1 | 50 |
| DMS-Nystatin | 0.25 | 100 |
| Rimocidin | 1.5 | 30 |
| DMS-Rimocidin | 2.5 | 50 |
| Amphotericin B | 0.03 | 5 |
| DMS-Amphotericin B | 0.08 | 5 |
| Mycoheptin | 0.05 | 15 |
| DMS-Mycoheptin | 0.2 | 65 |
| Candidin | 0.054 | 20 |
| DMS-Candidin | 0.15 | 70 |
| Candicidin | 0.005 | 2.5 |
| DMS-Candicidin | 0.005 | 15 |
| Aureofacin | 0.005 | 0.35 |
| DMS-Aureofacin | 0.003 | 15 |
| Levorin | 0.007 | 2.5 |
| DMS-Levorin | 0.009 | 20 |
| Trichomycin | 0.005 | 3 |
| DMS-Trichomycin | 0.01 | 10 |
| Perimycin | 0.002 | 5 |
| DMS-Perimycin | 0.003 | 12 | where - DMS - means the salt of N,N,N-trimethyl- ester of the antibiotic or the salt of N,N,N-trimethyl antibiotic.
IC$_{50}$ - means the concentration of the substance causing 50% inhibition of the growth of *Saccharomyces cerevisiae* cells in liquid standard medium determined spectrophotometrically at $\lambda = 600$ nm after 24 hours incubation in 28° C.
EH$_{50}$ - means the concentration of the substance causing in conditions 50% of hemoglobin determined spectrophotometrically at $\lambda = 550$ nm.

What we claim is:

1. An antibiotically-active water-soluble salt of a trimethylammonium derivative of a polyene macrolide having the general formula:

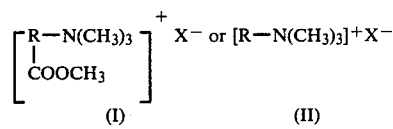

wherein R is the residue of a polyene macrolide selected from the group consisting of nystatin, polyfungin, amphotericin B, candicidin, pimaricin, trichomycin, levorin, rimocidin, candidin, aureofacin, perimycin and mycoheptin, and X is an anion of a salt selected from the group consisting of methylsulphate, sulphate, chloride, phosphate and acetate.

2. A process for the preparation of an antibiotically-active water soluble-salt of a trimethylammonium derivative of a polyene macrolide having the general formula:

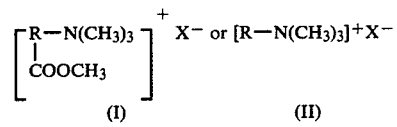

wherein R is the residue of a polyene macrolide selected from the group consisting of nystatin, polyfungin, amphotericin B, candicidin, pimaricin, trichomycin, levorin, rimocidin, candidin, auerofacin, perimycin and mycoheptin, and X is an anion of a salt selected from the group consisting of methylsulphate, sulphate, chloride, phosphate and acetate, which comprises reacting a solution of the polyene macrolide in an organic solvent with dimethylsulphate in the presence of a neutralizing agent at room temperature with continuous stirring until the reaction is substantially complete, precipitating the resulting methylsulphate of N,N,N-trimethyl polyene macrolide methyl ester of formula (I) or methylsulphate of N,N,N-trimethyl polyene macrolide of formula (II) by the addition of ethyl ether, dissolving the precipitate in butanol, washing the organic solvent with water and concentrating under reduced pressure the resulting solution of the desired product of formula (I) or (II) in the form of the methylsulphate salt thereof.

3. A process according to claim 2, in which the organic solvent is dimethylacetamide, dimethylformamide, dimethylsulphoxide or an aliphatic alcohol containing 1 to 5 carbon atoms.

4. A process according to claim 2, in which the neutralizing agent is sodium hydrogen carbonate.

* * * * *